(12) United States Patent
Ueda et al.

(10) Patent No.: US 11,858,142 B2
(45) Date of Patent: Jan. 2, 2024

(54) MANIPULATION SYSTEM AND DRIVING METHOD OF MANIPULATION SYSTEM

(71) Applicant: NSK LTD., Tokyo (JP)

(72) Inventors: Hiroki Ueda, Kanagawa (JP); Manabu Kishida, Kanagawa (JP); Nobuaki Tanaka, Kanagawa (JP)

(73) Assignee: NSK LTD., Tokyo (JP)

( * ) Notice: Subject to any disclaimer, the term of this patent is extended or adjusted under 35 U.S.C. 154(b) by 481 days.

(21) Appl. No.: 16/973,239

(22) PCT Filed: May 27, 2019

(86) PCT No.: PCT/JP2019/020859
§ 371 (c)(1),
(2) Date: Dec. 8, 2020

(87) PCT Pub. No.: WO2020/183741
PCT Pub. Date: Sep. 17, 2020

(65) Prior Publication Data
US 2021/0237268 A1 Aug. 5, 2021

(30) Foreign Application Priority Data
Mar. 8, 2019 (JP) .................................. 2019-043012

(51) Int. Cl.
*B25J 9/16* (2006.01)
*B25J 7/00* (2006.01)
(Continued)

(52) U.S. Cl.
CPC ............... *B25J 9/1651* (2013.01); *B25J 7/00* (2013.01); *B25J 9/1697* (2013.01); *C12M 1/00* (2013.01); *G02B 21/32* (2013.01); *G02B 21/36* (2013.01)

(58) Field of Classification Search
CPC . C12M 1/00; B25J 7/00; B25J 19/023; G02B 21/32; G02B 21/36; G05B 2219/39109
See application file for complete search history.

(56) References Cited

U.S. PATENT DOCUMENTS

2019/0381495 A1* 12/2019 Tanaka .................. B01L 3/0286
2020/0179005 A1*  6/2020 Matsumoto ............... B25J 7/00
2021/0215727 A1*  7/2021 Ueda ...................... G02B 21/26

FOREIGN PATENT DOCUMENTS

JP   2012-244910 A    12/2012
JP   2012244910 A  * 12/2012 ............ C12M 35/00
(Continued)

OTHER PUBLICATIONS

International Search Report of PCT/JP2019/020859 dated Aug. 20, 2019 [PCT/ISA/210].
(Continued)

*Primary Examiner* — Abby Y Lin
*Assistant Examiner* — Dylan Brandon Mooney
(74) *Attorney, Agent, or Firm* — Sughrue Mion, PLLC

(57) ABSTRACT

Provided are a manipulation system and a driving method of the manipulation system capable of performing manipulation efficiently and suitably while suppressing damage to a minute object at the time of manipulation regardless of the degree of skill and technique of an operator. A sample stage configured such that a minute object is placed thereon, a first manipulator including a first pipette for holding the minute object, a second manipulator including a second pipette for operating the minute object that is held on the first pipette, an imaging unit for imaging the minute object, and a controller that controls the sample stage, the first pipette, the second pipette, and the imaging unit are provided.

8 Claims, 6 Drawing Sheets

(51) Int. Cl.
*C12M 1/00* (2006.01)
*G02B 21/32* (2006.01)
*G02B 21/36* (2006.01)

(56) References Cited

FOREIGN PATENT DOCUMENTS

| JP | 2017-124452 A | | 7/2017 | | |
|----|---------------|---|--------|---|---|
| JP | 2017124452 A | * | 7/2017 | ............ | C12M 35/00 |

OTHER PUBLICATIONS

Written Opinion of PCT/JP2019/020859 dated Aug. 20, 2019 [PCT/ISA/237].

* cited by examiner

MANIPULATION SYSTEM AND DRIVING METHOD OF MANIPULATION SYSTEM

CROSS REFERENCE TO RELATED APPLICATIONS

This application is a National Stage of International Application No. PCT/JP2019/020859 filed on May 27, 2019, claiming priority based on Japanese Patent Application No. 2019-043012 filed on Mar. 8, 2019.

FIELD

The present invention relates to a manipulation system and a driving method of the manipulation system.

BACKGROUND

In a biotechnology field, a micromanipulation system for performing a fine operation on a minute object such as injecting a DNA solution or a cell into a cell or an ovum under microscope observation has been known. An injection operation is performed by piercing a manipulation pipette into a minute object while fixing the position of the minute object by a holding pipette for holding the minute object.

Patent Literature 1 discloses a technique that detects the position coordinates of a minute object from data of an acquired captured image and, based on a detection result, determines the position of a manipulation target.

CITATION LIST

Patent Literature

Patent Literature 1: Japanese Patent Application Laid-open No. 2017-124452 A

SUMMARY

Technical Problem

In the manipulation of the minute object, quantitatively detecting the position of the manipulation target and performing manipulation at an accurate position without damaging the minute object are desired.

The present invention has been made in view of the foregoing, and an object of the invention is to provide a manipulation system and a driving method of the manipulation system capable of performing manipulation efficiently and suitably while suppressing damage to the minute object at the time of manipulation, regardless of the degree of skill and technique of an operator.

Solution to Problem

A manipulation system according to an embodiment of the present invention comprising: a sample stage configured such that a minute object is placed thereon; a first manipulator including a first pipette for holding the minute object; a second manipulator including a second pipette for operating the minute object that is held on the first pipette; an imaging unit configured to image the minute object; and a controller configured to control the sample stage, the first pipette, the second pipette, and the imaging unit, wherein the controller moves a tip of the second pipette from a certain insertion start position of the minute object to a certain push-in position at a constant speed or a first acceleration, and after a predetermined time, moves the tip of the second pipette from the push-in position to a certain manipulation execution position at a second acceleration greater than the first acceleration.

Accordingly, because the minute object is pressed at low speed until the tip of the second pipette reaches the push-in position from coming in contact with the minute object, the minute object is not pierced by the second pipette but deformed. The sufficiently deformed minute object, by being pressed at high speed, results in local destruction due to an impact load and is pierced. Thus, the piercing can be performed easily without damaging other tissues of the minute object. As a result, regardless of the degree of skill and technique of an operator, manipulation can be performed efficiently and suitably while suppressing damage to the minute object at the time of manipulation.

The manipulation system according to an embodiment of the present invention, wherein the controller determines the manipulation execution position based on image data of the imaging unit. Accordingly, because the manipulation execution position is determined based on the captured image data, the manipulation can be performed on the minute object efficiently and suitably, regardless of the degree of skill and technique of the operator.

The manipulation system according to an embodiment of the present invention, wherein the controller determines the insertion start position based on image data of the imaging unit and the manipulation execution position. Accordingly, because the insertion start position is determined based on the captured image data and the manipulation execution position that is determined based on the image data, the minute object can be pierced efficiently and suitably, regardless of the degree of skill and technique of the operator.

The manipulation system according to an embodiment of the present invention, wherein the controller determines the push-in position based on image data of the imaging unit and the manipulation execution position. Accordingly, because the push-in position is determined based on the captured image data and the manipulation execution position that is determined based on the image data, the minute object can be pierced efficiently and suitably, regardless of the degree of skill and technique of the operator.

The manipulation system according to an embodiment of the present invention, wherein the minute object is a cell. Accordingly, because the cell membrane is pressed at low speed until the tip of the second pipette reaches the push-in position from coming in contact with the cell membrane of the cell, the cell membrane is not pierced by the second pipette but deformed. The cell membrane, when sufficiently pressed, is in a hardened state due to the tensile force. The cell membrane in a hardened state, by being pressed at high speed, results in local destruction due to an impact load and is pierced. Thus, the cell membrane can be pierced easily without damaging other tissues in the cell. As a result, regardless of the degree of skill and technique of the operator, manipulation can be performed efficiently and suitably while suppressing damage to the cell at the time of manipulation.

The manipulation system according to an embodiment of the present invention, wherein the controller detects a position of a nucleolus of the cell based on image data of the imaging unit. Accordingly, because the position of the nucleolus of the cell is detected based on the captured image data, the nucleolus can be detected efficiently and suitably, regardless of the degree of skill and technique of the operator.

The manipulation system according to an embodiment of the present invention, wherein the controller determines the manipulation execution position based on the position of the nucleolus. Accordingly, because the manipulation execution position is determined based on the position of the nucleolus detected from the captured image data, the manipulation can be performed on the minute object efficiently and suitably, regardless of the degree of skill and technique of the operator.

The manipulation system according to an embodiment of the present invention, wherein the manipulation execution position is outside the nucleolus. Accordingly, by setting the manipulation execution position outside the nucleolus, injection operation can be performed without coming in contact with the nucleolus with the tip of the second pipette when inserting the second pipette. Thus, in injection operation, damage to the cell can be suppressed.

The manipulation system according to an embodiment of the present invention, wherein the manipulation execution position is a position offset from a center of the nucleolus. Accordingly, the tip of the second pipette can be prevented from damaging the nucleolus when inserting the second pipette. Thus, in injection operation, damage to the cell can be suppressed.

The manipulation system according to an embodiment of the present invention, wherein a distance in an intersecting direction orthogonal to an insertion direction of the second pipette between a center of the nucleolus and the manipulation execution position is greater than a radius of the nucleolus. Accordingly, because the manipulation execution position can be set outside the nucleolus, injection operation can be performed without coming in contact with the nucleolus with the tip of the second pipette when inserting the second pipette. Thus, in injection operation, damage to the cell can be suppressed.

A driving method of a manipulation system according to an embodiment of the present invention including a sample stage configured such that a minute object is placed thereon, a first manipulator including a first pipette for holding the minute object, and a second manipulator including a second pipette for operating the minute object that is held on the first pipette, the driving method comprising: moving a tip of the second pipette to a certain insertion start position of the minute object; moving the tip of the second pipette from the insertion start position to a certain push-in position at a constant speed or a first acceleration; and after a predetermined time, moving the tip of the second pipette from the push-in position to a certain manipulation execution position at a second acceleration greater than the first acceleration.

Accordingly, because the minute object is pressed at low speed until the tip of the second pipette reaches the push-in position from coming in contact with the minute object, the minute object is not pierced by the second pipette but deformed. The sufficiently deformed minute object, by being pressed at high speed, results in local destruction due to an impact load and is pierced. Thus, the piercing can be performed easily without damaging other tissues of the minute object. As a result, regardless of the degree of skill and technique of the operator, manipulation can be performed efficiently and suitably while suppressing damage to the minute object at the time of manipulation.

Advantageous Effects of Invention

According to the present invention, regardless of the degree of skill and technique of the operator, manipulation can be performed efficiently and suitably while suppressing damage to the minute object at the time of manipulation.

DESCRIPTION OF EMBODIMENT

With reference to the accompanying drawings, a mode for implementing the present invention (exemplary embodiment) will be described in detail. The present invention is not intended to be limited by the content described in the following embodiment. Furthermore, constituent elements described in the following include elements easily achieved by a person skilled in the art or elements being substantially the same as the constituent elements. Moreover, the constituent elements described in the following can be combined as appropriate.

Figure 1:
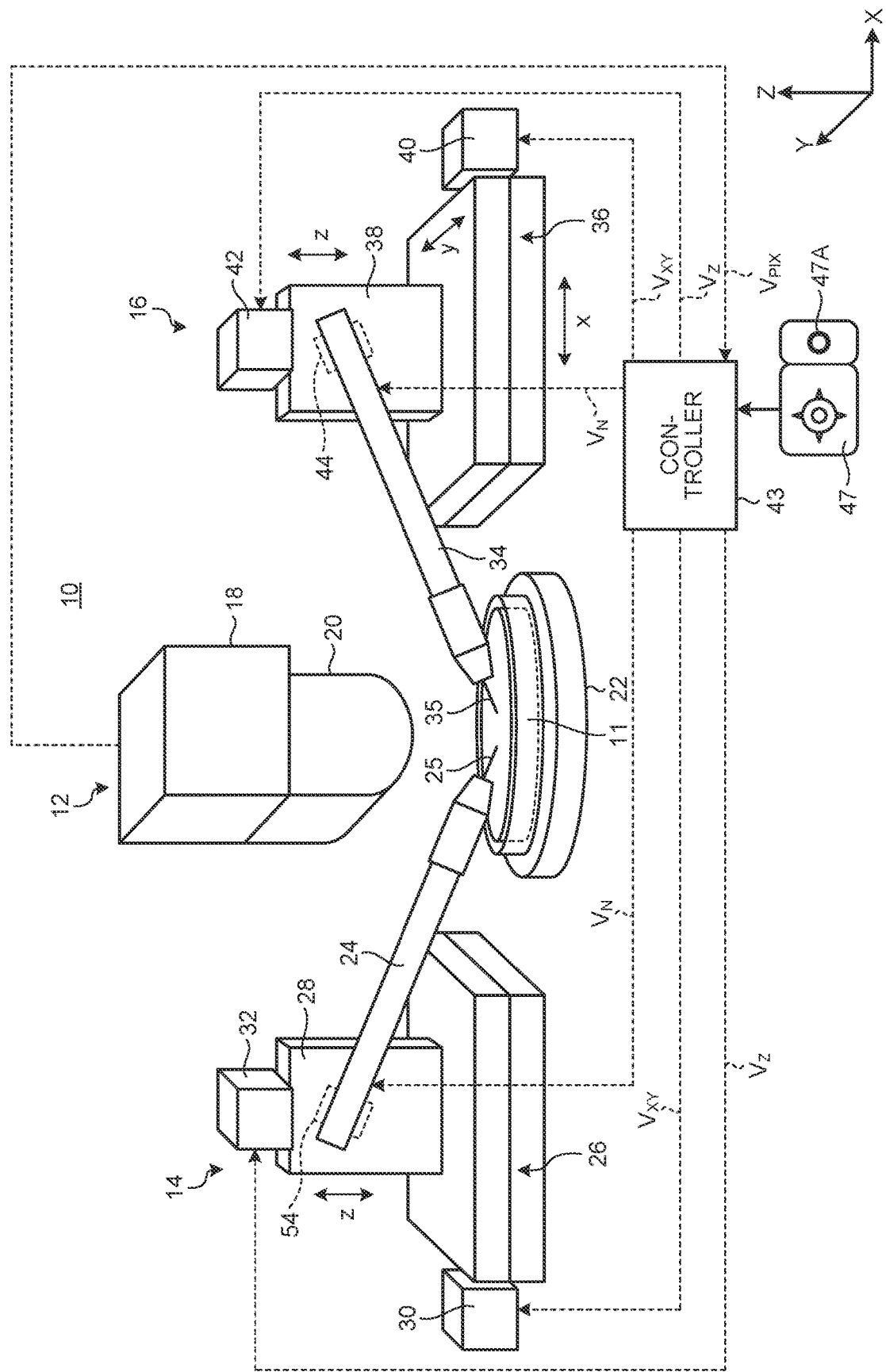
FIG. 1 is a diagram schematically illustrating a configuration of a manipulation system according to an embodiment.

FIG. 1 is a diagram schematically illustrating a configuration of a manipulation system according to the embodiment. A manipulation system 10 is a system to manipulate a sample, which is a minute object, under microscope observation. In FIG. 1, the manipulation system 10 includes a microscope unit 12, a first manipulator 14, a second manipulator 16, and a controller (control device) 43 that controls the manipulation system 10. The first manipulator 14 and the second manipulator 16 are separately arranged such that the first manipulator 14 is on one side of the microscope unit 12 and the second manipulator 14 on the other side of the microscope unit 12.

The microscope unit 12 includes a camera 18 including an imaging element, a microscope 20, and a sample stage 22. The sample stage 22 can support a sample holding member 11 such as a petri dish, and the microscope 20 is arranged directly above the sample holding member 11. The microscope unit 12 has a structure in which the microscope 20 and the camera 18 are integrated, and includes a light source (depiction omitted) that emits light toward the sample holding member 11. The camera 18 may be provided separately from the microscope 20.

In the sample holding member 11, a solution containing a sample is accommodated. The solution is, for example, paraffin oil. When the sample of the sample holding member 11 is irradiated with light and light reflected by the samples of the sample holding member 11 is incident on the microscope 20, an optical image of the sample is magnified by the microscope 20 and thereafter captured by the camera 18. Based on the image captured by the camera 18, the sample can be observed.

As illustrated in FIG. 1, the first manipulator 14 includes a first pipette holding member 24, an X-Y axis table 26, a Z-axis table 28, a drive device 30 that drives the X-Y axis table 26, and a drive device 32 that drives the Z-axis table 28. The first manipulator 14 is a manipulator having a triaxial configuration, i.e., an X-Y-Z axis configuration. In the present embodiment, a direction in the horizontal plane is referred to as an X-axis direction, a direction that intersects with the X-axis direction is referred to as a Y-axis direction, and a direction that intersects with each of the X-axis direction and the Y-axis direction (i.e., vertical direction) is referred to as a Z-axis direction.

The X-Y axis table 26 is movable in the X-axis direction or the Y-axis direction by drive of the drive device 30. The Z-axis table 28 is arranged to be movable up and down on the X-Y axis table 26 and is movable in the Z-axis direction by drive of the drive device 32. The drive devices 30 and 32 are connected to the controller 43.

The first pipette holding member 24 is coupled to the Z-axis table 28, and a first pipette 25, which is a capillary tip, is attached at a front end. The first pipette holding member 24 can move in accordance with the movement of the X-Y axis table 26 and the Z-axis table 28 in a three-dimensional space as a moving area, and can hold the sample accommodated in the sample holding member 11 via the first pipette 25. That is, the first manipulator 14 is a holding manipulator used for holding a minute object, and the first pipette 25 is a holding pipette used as a holding means of the minute object.

The second manipulator 16 illustrated in FIG. 1 includes a second pipette holding member 34, an X-Y axis table 36, a Z-axis table 38, a drive device 40 that drives the X-Y axis table 36, and a drive device 42 that drives the Z-axis table 38. The second manipulator 16 is a manipulator having the triaxial configuration, i.e., the X-Y-Z axis configuration.

The X-Y axis table 36 is movable in the X-axis direction or the Y-axis direction by drive of the drive device 40. The Z-axis table 38 is arranged to be movable up and down on the X-Y axis table 36 and is movable in the Z-axis direction by drive of the drive device 42. The drive devices 40 and 42 are connected to the controller 43.

The second pipette holding member 34 is coupled to the Z-axis table 38, and a second pipette 35 made of glass is attached at the front end. The second pipette holding member 34 can move in accordance with the movement of the X-Y axis table 36 and the Z-axis table 38 in a three-dimensional space as a moving area, and can artificially manipulate the sample accommodated in the sample holding member 11. That is, the second manipulator 16 is an operation manipulator used for the manipulation (such as injection operation of a DNA solution and piercing operation) of the minute object, and the second pipette 35 is an injection pipette used as an injection operation means of the minute object.

The X-Y axis table 36 and the Z-axis table 38 are configured as a coarse-motion mechanism (three-dimensional moving table) that drives the second pipette holding member 34 to coarsely move to a manipulation position of the sample or the like that is accommodated in the sample holding member 11. Further, a micro-motion mechanism 44 as a nano-positioner is provided at a coupling portion between the Z-axis table 38 and the second pipette holding member 34. The micro-motion mechanism 44 is configured to support the second pipette holding member 34 movably in a longitudinal direction (axial direction) thereof and also to micro-drive the second pipette holding member 34 along the longitudinal direction (axial direction) thereof.

Figure 2:
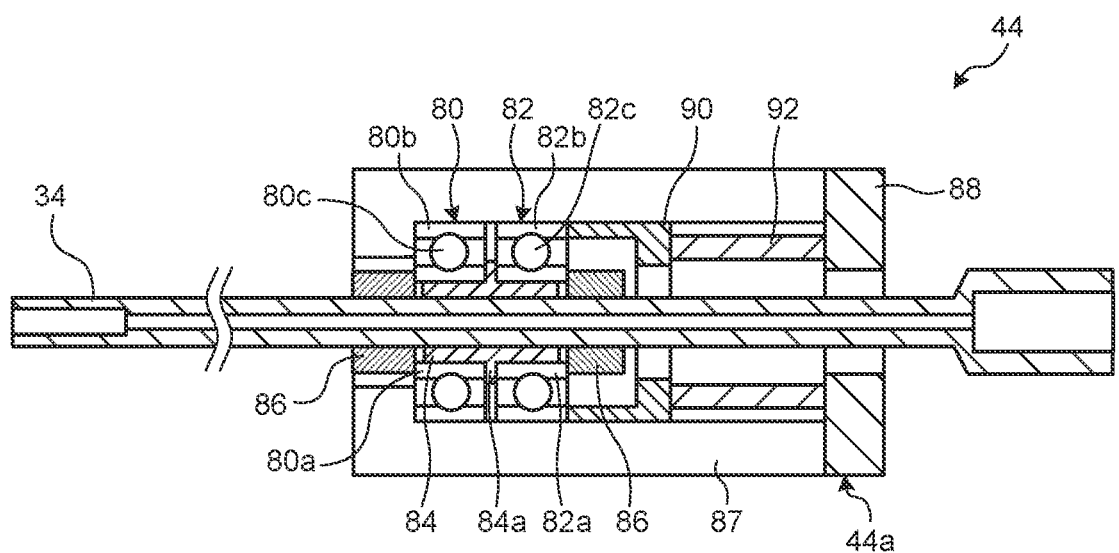
FIG. 2 is a cross-sectional view illustrating one example of a micro-motion mechanism.

FIG. 2 is a cross-sectional view illustrating one example of the micro-motion mechanism. As illustrated in FIG. 2, the micro-motion mechanism 44 includes a piezoelectric actuator 44a that drives the second pipette holding member 34 as a driving target. The piezoelectric actuator 44a includes a cylindrical housing 87, roller bearings 80 and 82 provided inside the housing 87, and a piezoelectric element 92. The second pipette holding member 34 is inserted through the housing 87 in the axial direction. The roller bearings 80 and 82 rotatably support the second pipette holding member 34. The piezoelectric element 92 expands and contracts along the longitudinal direction of the second pipette holding member 34 in accordance with a voltage applied thereto. The second pipette 35 (see FIG. 1) is attached and fixed to the second pipette holding member 34 on a front end side (left side in FIG. 2).

The second pipette holding member 34 is supported by the housing 87 via the roller bearings 80 and 82. The roller bearing 80 includes an inner ring 80a, an outer ring 80b, and balls 80c provided between the inner ring 80a and the outer ring 80b. The roller bearing 82 includes an inner ring 82a, an outer ring 82b, and balls 82c provided between the inner ring 82a and the outer ring 82b. Each of the outer rings 80b and 82b is fixed to the inner circumferential surface of the housing 87, and each of the inner rings 80a and 82a is fixed to the outer circumferential surface of the second pipette holding member 34 via a hollow member 84. In this manner, the roller bearings 80 and 82 rotatably support the second pipette holding member 34.

A flange portion 84a projecting outward in a radial direction is provided at a substantially central portion in the axial direction of the hollow member 84. The roller bearing 80 is arranged on the front end side in the axial direction of the second pipette holding member 34 with respect to the flange portion 84a, and the roller bearing 82 is arranged on a rear end side with respect to the flange portion 84a. The inner ring 80a of the roller bearing 80 and the inner ring 82a of the roller bearing 82 are arranged so as to sandwich the flange portion 84a serving as an inner ring spacer. The second pipette holding member 34 is threaded on the outer circumferential surface, and a locknut 86 and a locknut 86 are screwed to the second pipette holding member 34 from the front end side of the inner ring 80a and the rear end side of the inner ring 82a, respectively. Thus, the positions in the axial direction of the roller bearings 80 and 82 are fixed.

An annular spacer 90 is arranged on the rear end side in the axial direction of the outer ring 82b coaxially with the roller bearings 80 and 82. On the rear end side in the axial direction of the spacer 90, the annular piezoelectric element 92 is arranged substantially coaxially with the spacer 90. On the further rear end side in the axial direction, a lid 88 of the housing 87 is arranged. The lid 88 is for fixing the piezoelectric element 92 in the axial direction and has a hole portion through which the second pipette holding member 34 is inserted. The lid 88 may be fastened to the side surface of the housing 87, for example, by bolts, which are not illustrated. The piezoelectric elements 92, having a rod-like shape or a prismatic shape, may be arranged in a substantially regular interval in the circumferential direction of the spacer 90, or the piezoelectric element 92 may have a square tube having a hole portion through which the second pipette holding member 34 is inserted.

The piezoelectric element 92 is in contact with the roller bearing 82 via the spacer 90. The piezoelectric element 92 is connected to the controller 43 as a control circuit via lead wires (not illustrated). The piezoelectric element 92 is configured to expand and contract along the axial direction of the second pipette holding member 34 in response to a voltage applied from the controller 43, and finely move the second pipette holding member 34 along the axial direction thereof. When the second pipette holding member 34 finely moves along the axial direction, this fine movement is transmitted to the second pipette 35 (see FIG. 1) and the position of the second pipette 35 is finely adjusted. Further, when the second pipette holding member 34 vibrates in the axial direction by the piezoelectric element 92, the second pipette 35 also vibrates in the axial direction. In this manner, the micro-motion mechanism 44 enables a more accurate operation in manipulating (injection operation of a DNA solution or a cell, piercing operation, and the like) a minute object, and improvement in a piercing action by the piezoelectric element 92 can be achieved.

While it has been described that the above-described micro-motion mechanism 44 is provided on the second manipulator 16 for manipulating a minute object, a micro-motion mechanism 54, which is the same as the micro-motion mechanism 44, may be provided on the first manipulator 14 for fixing the minute object as illustrated in FIG. 1, or it can be omitted.

Figure 3:
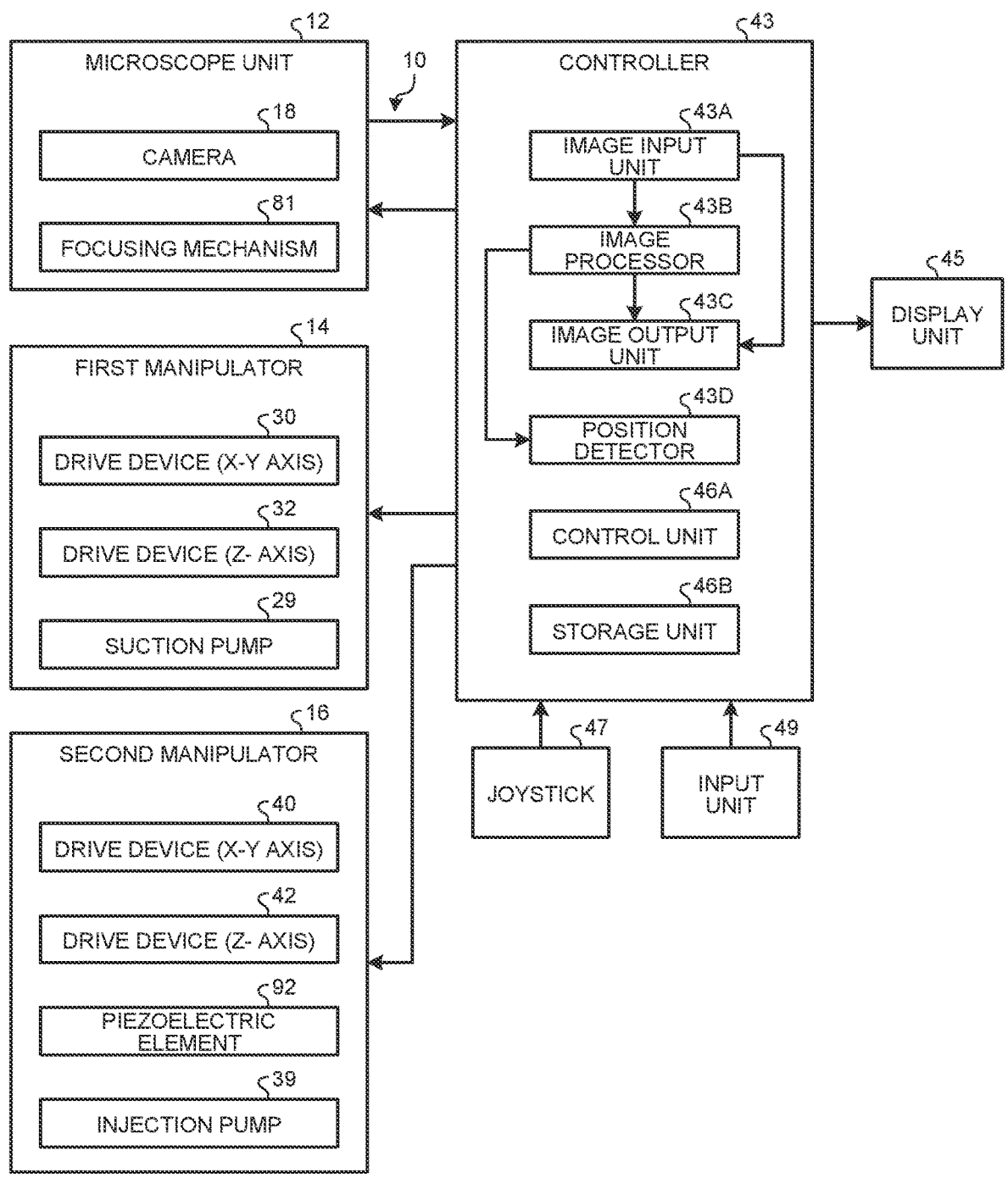
FIG. 3 is a control block diagram of the manipulation system.

Subsequently, the control of the manipulation system 10 performed by the controller 43 will be described with reference to FIG. 3. FIG. 3 is a control block diagram of the manipulation system.

The controller 43 includes hardware resources such as a CPU (central processing unit) as an arithmetic means, and a hard disk, a RAM (random access memory), and a ROM (read-only memory) as a storage means. The controller 43 performs various calculations based on a predetermined program stored in a storage unit 46B, and outputs drive signals in accordance with the calculation result so that a control unit 46A performs various controls.

The control unit 46A controls a focusing mechanism 81 of the microscope unit 12, the drive device 30, the drive device 32, and a suction pump 29 of the first manipulator 14, the drive device 40, the drive device 42, the piezoelectric element 92, and an injection pump 39 of the second manipulator 16, and outputs respective drive signals via drivers and amplifiers provided as needed. The control unit 46A supplies corresponding drive signals $V_{xy}$ and $V_z$ (see FIG. 1) to the drive devices 30, 32, 40, and 42. The drive devices 30, 32, 40, and 42 performs drive in the X-Y-Z-axis directions based on the corresponding drive signals $V_{xy}$ and $V_z$. The control unit 46A may supply a nano-positioner control signal $V_N$ (see FIG. 1) to the micro-motion mechanism 44 to control the micro-motion mechanism 44.

The controller 43 is connected to a joystick 47 as an information input means and to an input unit 49 such as a keyboard, a mouse, and a touch panel. The controller 43 is further connected to a display unit 45 such as a liquid crystal panel. Microscope images acquired by the camera 18 and various control screens are displayed on the display unit 45. When a touch panel is used as the input unit 49, the touch panel may be used so as to overlap the display screen of the display unit 45, and an operator may perform an input operation while checking the display image of the display unit 45.

A known joystick can be used for the joystick 47. The joystick 47 includes a base and a handle portion standing erect from the base, and operating the handle portion to tilt can cause the drive devices 30 and 40 to perform X-Y drive and twisting the handle portion can cause the drive devices 32 and 42 to perform Z-drive. The joystick 47 may include a button 47A for operating each drive of the suction pump 29, the piezoelectric element 92, and the injection pump 39.

As illustrated in FIG. 3, the controller 43 further includes an image input unit 43A, an image processor 43B, an image output unit 43C, and a position detector 43D. An image signal Vpix (see FIG. 1) imaged by the camera through the microscope 20 is input to the image input unit 43A. The image processor 43B receives the image signal from the image input unit 43A and performs image processing. The image output unit 43C outputs image information subjected to the image processing by the image processor 43B to the display unit 45. The position detector 43D can detect, based on the image information after image processing, the position of a cell and the like, which is a minute object imaged by the camera 18, and the position of a nucleus of the cell that is a manipulation target on which an injection operation by the second pipette 35 is performed. The position detector 43D can detect the presence of the cells and the like in the imaging area of the camera 18 based on the image information. Further, the position detector 43D may detect the positions of the first pipette 25 and the second pipette 35. The image input unit 43A, the image processor 43B, the image output unit 43C, and the position detector 43D are controlled by the control unit 46A.

The control unit 46A controls, based on the positional information from the position detector 43D and the information on the presence of the cells and the like, the first manipulator 14 and the second manipulator 16. In the present embodiment, the control unit 46A automatically drives the first manipulator 14 and the second manipulator 16 in a predetermined sequence. Such sequence drive is performed by the control unit 46A sequentially outputting the corresponding drive signals based on the calculation result of the CPU by a predetermined program stored in the storage unit 46B in advance.

Next, with reference to FIG. 4 and FIG. 5, a method of detecting a manipulation target of a sample that is a minute object and a method of determining a manipulation execution position IJ, an insertion start position D of the second pipette 35, and a push-in position P will be described. In the present embodiment, the samples are cells 100. The cells 100 are pre-nucleus fertilized ova. The manipulation to the cell 100 is an injection operation of a DNA solution. In the present embodiment, the insertion direction of the second pipette 35 to the cell 100 is parallel to the X-axis direction. An intersecting direction orthogonal to the insertion direction is parallel to the Y-axis direction.

Figure 4:
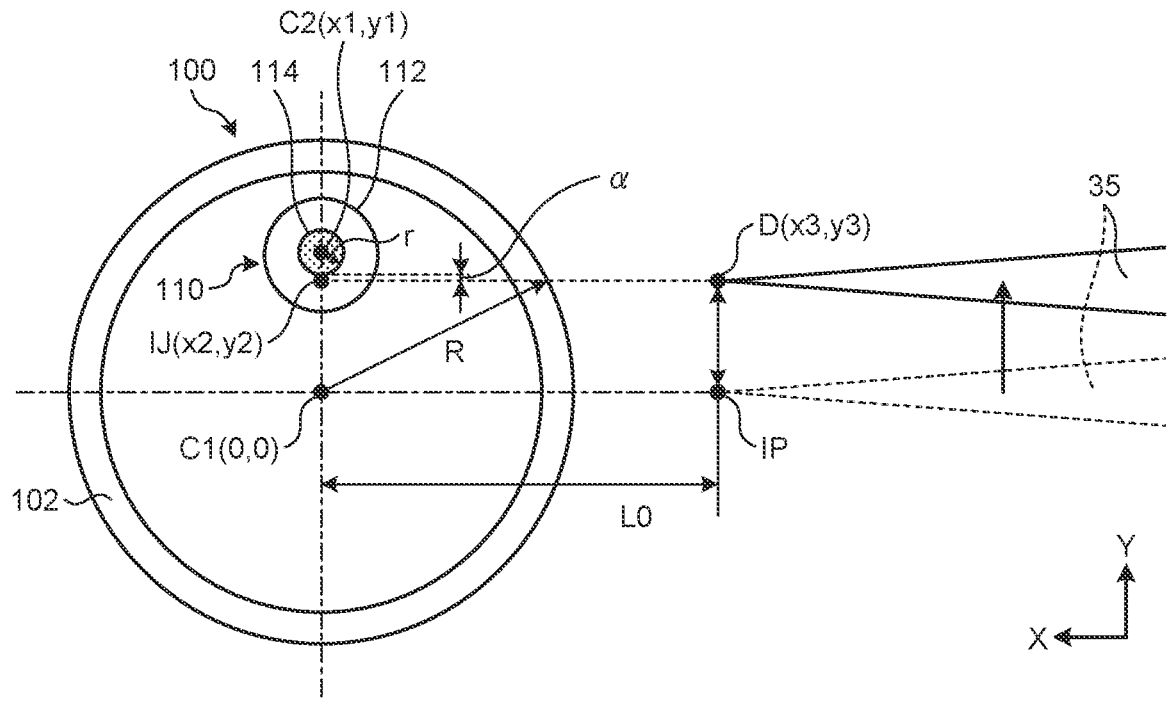
FIG. 4 is a schematic diagram illustrating one example of a cell of a manipulation target and a nucleus.
Figure 5:
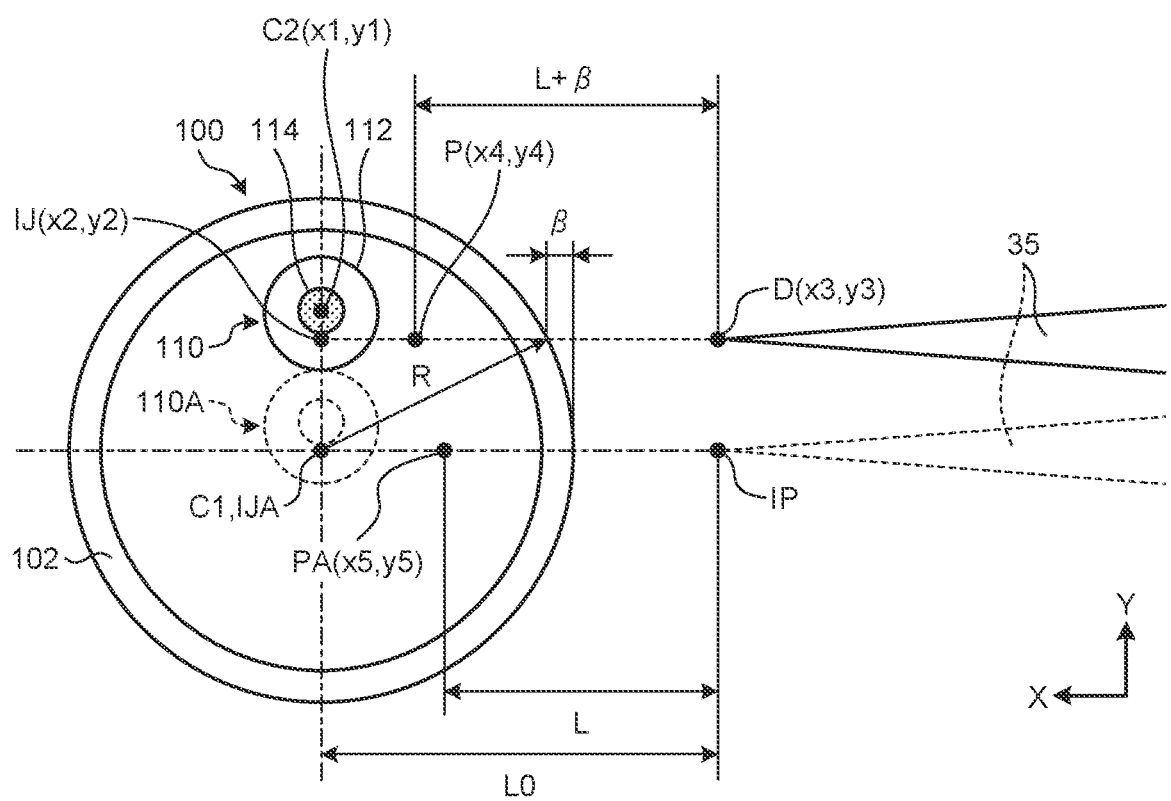
FIG. 5 is a schematic diagram illustrating one example of the cell of the manipulation target and the nucleus.

FIG. 4 and FIG. 5 are schematic diagrams illustrating one example of the cell of the manipulation target and the nucleus. The cells 100 are accommodated in the sample holding member 11. In the present embodiment, the sample holding member 11 includes an untreated cell region where untreated cells 100 are placed, a successful cell region where the cells 100 of successful manipulation are placed, and a failure cell region where the cells 100 of failed manipulation are placed. The cell 100 includes a cell membrane 102 and nuclei 110. The cell membrane 102 is a biological membrane that separates the inside and the outside of the cell 100. The cell membrane 102 has fluidity and, by contact with the tip of the second pipette 35, deforms and hardens. The nucleolus 110 is present inside the cell 100 covered with the cell membrane 102. The nucleus 110 includes a nuclear membrane 112 and a nucleolus 114. The nucleolus 114 is present inside the nucleus 110 covered with the nuclear membrane 112. The cell 100 is, in a state of being held by the first pipette 25, subjected to the injection operation by the second pipette 35.

In the injection of a DNA solution and the like, the DNA solution and the like needs to be injected into the inside of the nuclear membrane 112. Because the nuclear membrane 112 is low in contrast and the shape is indefinite, detection by common image processing methods such as edge extraction processing and the like is difficult. Thus, the nucleolus 114 of higher contrast than the nuclear membrane 112 is detected, and based on the position of the nucleolus 114, the manipulation execution position IJ of injection is determined.

The image data of the cells 100 is imaged by the camera 18 illustrated in FIG. 3. The image data of the cells 100 imaged by the camera 18 is sent to the image processor 43B from the image input unit 43A as an image signal. The image processor 43B performs image processing on the image data of the cells 100. The image processor 43B performs binarization processing and filter processing on the image signal received from the image input unit 43A, in order to detect the positions and shapes of the cells 100 and the nucleoli 114. The image processor 43B gray-scales the image signal and, based on a predetermined threshold value, converts the grayscale image into a monochrome image. Then, based on the monochrome image obtained by the binarization processing and the filter processing, the image processor 43B performs edge extraction processing and pattern matching. The position detector 43D can, based on the processing result thereof, detect the positions and shapes of the cells 100 and the nucleoli 114. Specifically, the controller 43 detects the radius R of the cell 100, the center C1 of the cell 100, the radius r of the nucleolus 114, and the center C2 of the nucleolus 114 based on the image data.

The controller 43 moves, based on the detection result, the first pipette 25, thereby moving the center C1 of the cell 100 to a preset origin (0, 0). The controller 43 may define the coordinates of an X-Y plane of the center C1 of the cell 100 as the origin (0, 0). The controller 43 calculates, based on the positions of the center C1 of the cell 100 and the center C2 of the nucleolus 114 in the detection result, the coordinates (x1, y1) of the center C2 of the nucleolus 114. In the present embodiment, x1=0.

The manipulation execution position IJ of injection is a position of the tip of the second pipette 35 when the second pipette 35 performs an injection operation on the cell 100. The coordinates (x2, y2) of the manipulation execution position IJ of injection are determined by the coordinates (x1, y1) of the center C2 of the nucleolus 114, the radius r of the nucleolus 114, and an offset amount α. The offset amount α is an arbitrary setting value that is preset. The coordinates (x2, y2) of the manipulation execution position IJ are, with respect to the coordinates (x1, y1) of the center C2 of the nucleolus 114, a position moved by (r+α) in the Y-axis direction toward the center C1 of the cell 100. The X coordinate x2 of the manipulation execution position IJ is calculated by x2=x1. In the present embodiment, x2=0. The Y coordinate y2 of the manipulation execution position IJ, when y1≥0, is calculated by y2=y1−(r+α). The Y coordinate y2 of the manipulation execution position IJ, when y1<0, is calculated by y2=y1+(r+α).

The insertion start position D of the second pipette 35 is a position where an insertion operation of the second pipette 35 to the cell 100 is started. The second pipette 35 is inserted toward the insertion start position D and in parallel with the X-axis. As illustrated in FIG. 4, the coordinates (x3, y3) of the insertion start position D of the second pipette 35 are determined by the coordinates (x2, y2) of the manipulation execution position IJ and an initial distance L0. The initial distance L0 is the distance in the X-axis direction between the center C1 of the cell 100 and an initial position IP of the tip of the second pipette 35. The initial distance L0 is greater than the radius R of the cell 100. The Y coordinate y3 of the insertion start position D is calculated by y3=y2. The X coordinate x3 of the insertion start position D is calculated by x3=−L0.

The push-in position P of the second pipette 35 is a position of the tip of the second pipette 35 immediately before piercing the cell membrane 102 of the cell 100 with the tip of the second pipette 35. The push-in position P is on the inner side of the cell membrane 102 in an initial shape of the cell 100. The cell membrane 102 is pressed and deformed by the second pipette 35 until the tip of the second pipette 35 reaches the push-in position P from coming in contact with the cell membrane 102. As illustrated in FIG. 5, the coordinates (x4, y4) of the push-in position P of the second pipette 35 are determined by the coordinates (x2, y2) of the manipulation execution position IJ, the coordinates (x3, y3) of the insertion start position D, a predetermined push-in amount L, and a predetermined offset amount β. The push-in amount L is an arbitrary setting value that is preset. The offset amount β is a value calculated in accordance with the positions of the Y coordinates y2 and y3 of the manipulation execution position IJ and the insertion start position D, respectively. The coordinates (x4, y4) of the push-in position P is, with respect to the coordinates (x3, y3) of the insertion start position D, a position moved by (L+β) in the X-axis direction toward the manipulation execution position IJ. The Y coordinate y4 of the push-in position P is calculated by y4=y2=y3. The X coordinate x4 of the push-in position P is calculated by x4=−L0+(L+β). The offset amount β is calculated by β=y4*tan{sin^−1(y4/R)}.

Like a nucleus 110A illustrated in FIG. 5, when the coordinates of a manipulation execution position IJA coincide with the center C1 of the cell 100, the offset amount β is β=0. Thus, the coordinates (x5, y5) of a push-in position PA are calculated by x5=−L0+L and y5=0.

Next, a driving method of the manipulation system 10 will be described. Before starting the operation of the manipulation system 10, an operator first arranges the first pipette 25 and the second pipette 35 within the field of view of the camera 18 illustrated in FIG. 1. In this case, the height of the tip of the first pipette 25 is set to a position slightly above the bottom surface of the sample holding member 11. The operator then, by using the focusing mechanism 81 of the microscope 20, sets a focus on the first pipette 25. The operator adjusts, in a state where the focus is set on the first pipette 25, the height of the second pipette 35 so as to be focused on. The operator then moves the sample stage 22 so that the periphery of the cell 100 in the sample holding member 11 overlaps with the field of view of the camera 18. The operator further confirms that the cell 100 does not move even if the tip of the first pipette 25 is brought close to the cell 100. This is to confirm that the suction pump 29 illustrated in FIG. 3 is in an equilibrium state. With the foregoing preparation, the cell 100 is placed in the vicinity of the first pipette 25 and the second pipette 35.

Figure 6:
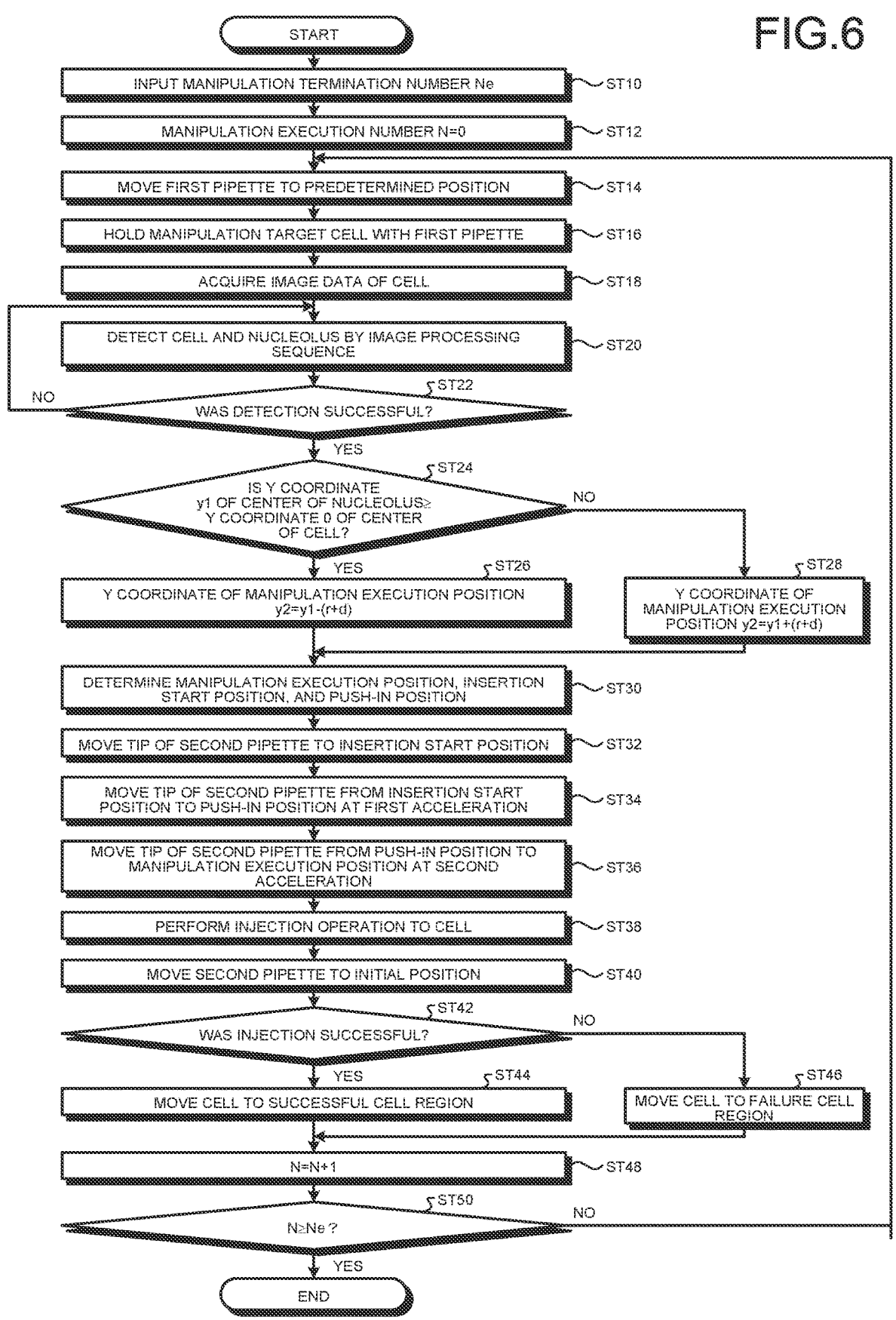
FIG. 6 is a flowchart illustrating one example of the operation of the manipulation system of the embodiment.
Figure 7:
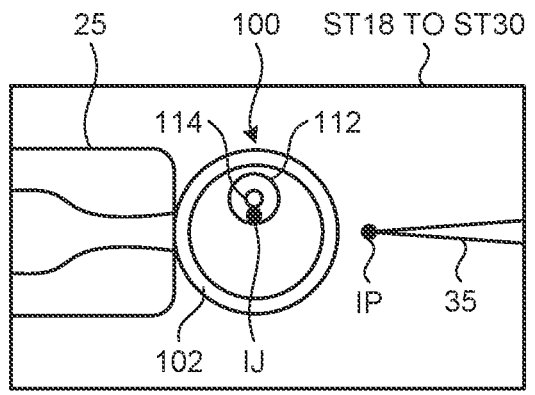
FIG. 7 is an explanatory diagram for explaining the operation of the manipulation system of the embodiment.
Figure 7:
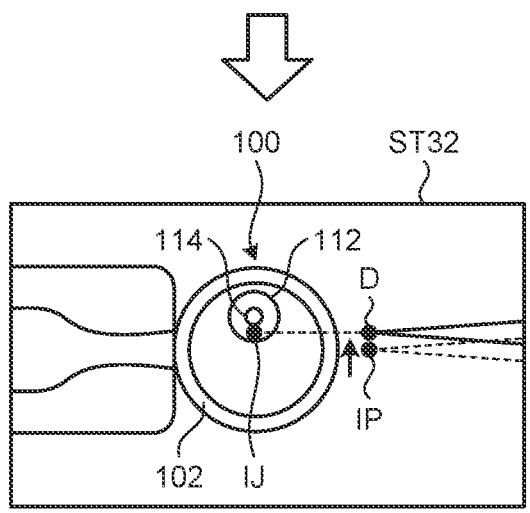
Figure 7:
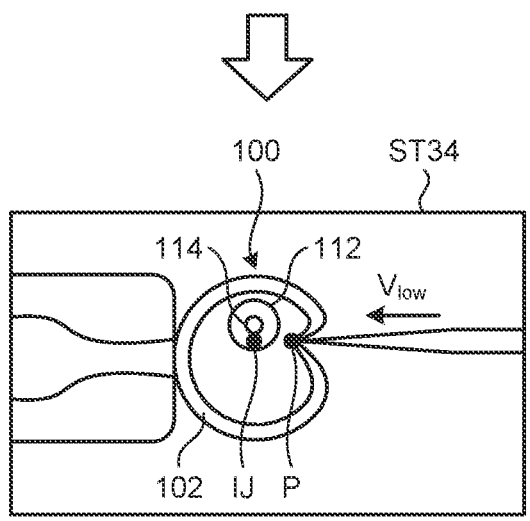
Figure 7:
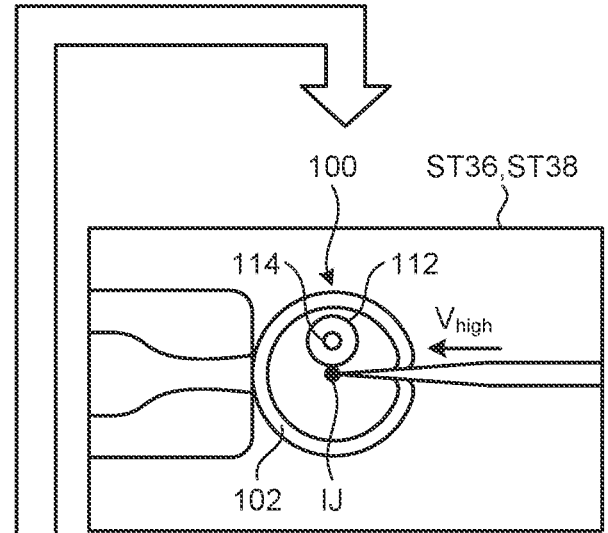
Figure 7:
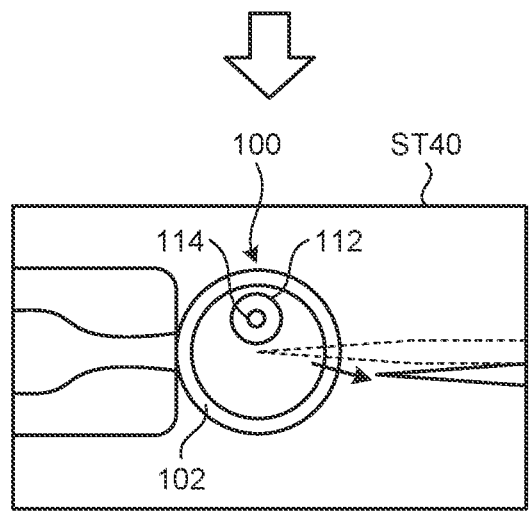
Figure 7:
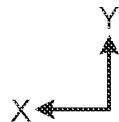

FIG. 6 is a flowchart illustrating one example of the operation of the manipulation system of the embodiment. FIG. 7 is an explanatory diagram explaining the operation of the manipulation system of the embodiment. The manipulation system 10, for a plurality of cells 100 placed in the sample holding member 11, performs manipulation for each piece of the cells 100 and repeatedly performs the manipulation on the multiple cells 100. The controller 43 performs the manipulation on the multiple cells 100 automatically. The automatic manipulation by the manipulation system 10 is started by pressing a start button on PC software, for example.

First, at Step ST10, the operator, after the manipulation system 10 has performed the manipulation multiple times, sets a manipulation termination number Ne that is the number of times to end the manipulation to the control unit 46A of the controller 43 via the input unit 49 illustrated in FIG. 3. Because the manipulation is performed for each piece of the cells 100, the manipulation termination number Ne is the number of cells 100 to perform manipulation. When the manipulation termination number Ne is input to the control unit 46A, at Step ST12, the control unit 46A sets the manipulation execution number N that is the value of a counter of the number of operations that have been performed to N=0, and stores it in the storage unit 46B of the controller 43.

Then, the image processor 43B of the controller 43 performs image processing on the image data imaged by the camera 18 through the microscope 20. The position detector 43D of the controller 43 detects, by image processing, the position coordinates of the tip center of the first pipette 25 on the screen of the camera 18 and the position coordinates of the tip center of the second pipette 35. At Step ST14, the control unit 46A moves, by driving the first manipulator 14, the first pipette 25 to a predetermined position on the basis of the detection result. The predetermined position is a position where the tip center of the first pipette 25 faces the cell 100 of the manipulation target.

Subsequently, at Step ST16, the control unit 46A drives the suction pump 29 of the first manipulator 14 to perform suction of the first pipette 25. When the suction pump 29 is driven, the pressure in the first pipette 25 becomes negative, and a flow of the solution of the sample holding member 11 arises toward the opening of the first pipette 25. The cell 100 is sucked together with the solution, and is adsorbed to the tip of the first pipette 25 and held. In this case, in order to confirm whether the cell 100 is being held, it may be determined by detecting, by image processing, whether the cell 100 is located in the vicinity of the tip of the first pipette 25.

Then, at Step ST18, the image processor 43B acquires image data of the cell 100. At Step ST20, the position detector 43D detects, based on the acquired image data, the positions and shapes of the cell 100 and the nucleolus 114 by an image processing sequence. At Step ST22, the position detector 43D determines whether the nucleolus 114 has been detected. At Step ST22, when determined that the nucleolus 114 has not been detected (No at Step ST22), the process returns to Step ST20 and the image processor 43B detects the positions and shapes of the cell 100 and the nucleolus 114 again by the image sequence. At Step ST22, when determined that the nucleolus 114 has not been detected, the process may return to Step ST18 and the image processor 43B may acquire the image data of the cell 100 again. At Step ST18, before acquiring the image data again, the control unit 46A may change the posture of the cell 100 by temporarily releasing the holding of the cell 100 by the first pipette 25.

At Step ST22, when determined that the nucleolus 114 has been detected (Yes at Step ST22), the control unit 46A calculates the coordinates (x1, y1) of the center C2 of the nucleolus 114. In the present embodiment, x1=0. At Step ST24, the control unit 46A determines whether the Y coordinate y1 of the center C2 of the nucleolus 114 is greater than or equal to the Y coordinate 0 of the center C1 of the cell 100. At Step ST24, when determined that the Y coordinate y1 of the center C2 of the nucleolus 114 is greater than or equal to the Y coordinate 0 of the center C1 of the cell 100, at Step ST26, the Y coordinate y2 of the manipulation execution position IJ is calculated by y2=y1−(r+α). At Step ST24, when determined that the Y coordinate y1 of the center C2 of the nucleolus 114 is smaller than the Y coordinate 0 of the center C1 of the cell 100, at Step ST28, the Y coordinate y2 of the manipulation execution position IJ is calculated by y2=y1+(r+α).

After calculating the Y coordinate y2 of the manipulation execution position IJ at Step ST26 and Step ST28, at Step ST30, the control unit 46A determines the manipulation execution position IJ, the insertion start position D, and the push-in position P. Specifically, the control unit 46A calculates the coordinates (x2, y2) of the manipulation execution position IJ, the coordinates (x3, y3) of the insertion start position D, and the coordinates (x4, y4) of the push-in position P and sets the moving path of the second pipette 35.

Then, at Step ST32, the control unit 46A moves the tip of the second pipette 35 to the insertion start position D. Because the initial position IP of the second pipette 35 and the insertion start position D have the same X coordinate, the second pipette 35 is translated in the Y-axis direction. The tip of the second pipette 35 faces the manipulation execution position IJ.

Then, at Step ST34, the control unit 46A moves the tip of the second pipette 35 from the insertion start position D to the push-in position P at a first acceleration $V_{low}$. The first acceleration $V_{low}$ is low acceleration or ultra-low acceleration. The control unit 46A may move the tip of the second pipette 35 at a constant speed from the insertion start position D to the push-in position P. Because the insertion start position D and the push-in position P have the same Y coordinate, the second pipette 35 is translated in the X-axis direction. Until the tip of the second pipette 35 reaches the push-in position P from coming in contact with the cell membrane 102, the cell membrane 102 is not pierced by the second pipette 35 but is pressed and deformed. As a result, the cell membrane 102 is given a tensile force. The cell membrane 102, when sufficiently pressed, is in a hardened state due to the tensile force. The second pipette 35 may, after Step ST34, before Step ST36, wait at the push-in position P for a predetermined time.

Then, at Step ST36, the control unit 46A moves the tip of the second pipette 35 from the push-in position P to the manipulation execution position IJ at a second acceleration $V_{high}$. The second acceleration $V_{high}$ is at least greater than the first acceleration $V_{low}$. The second acceleration $V_{high}$ is high acceleration. Because the push-in position P and the manipulation execution position IJ have the same Y coordinate, the second pipette 35 is translated in the X-axis direction. Because the cell membrane 102 is in a hardened state at Step ST34, the cell membrane 102 results, by moving the second pipette 35 at high speed, in local destruction due to an impact load and is pierced. The tip of the second pipette 35 is inserted into the cell membrane 102. The tip of the second pipette 35 is inserted into the nuclear membrane 112.

Then, at Step ST38, the control unit 46A drives the injection pump 39 of the second manipulator 16 and performs the injection operation of a DNA solution and the like on the cell 100. The control unit 46A may perform the injection operation, by driving the injection pump 39 for a preset time, for example. The image processor 43B may determine, by performing image processing during the injection operation and detecting a bulge of the nuclear membrane 112, whether the injection of a DNA solution and the like has been completed. After performing the injection operation, at Step ST40, the control unit 46A moves the second pipette 35 to the initial position IP. Specifically, the second pipette 35 is pulled out from the cell 100 by moving in the X-axis direction, and thereafter, returns to the initial position IP by moving in the Y-axis direction.

Subsequently, at Step ST42, the control unit 46A determines whether the injection operation was successful. At Step ST42, when determined that the injection operation was successful (Yes at Step ST42), the control unit 46A drives the sample stage 22 and moves the cell 100 after injection operation to the successful cell region. The control unit 46A stops the suction pump 29 of the first manipulator 14 and stops the suction of the first pipette 25. This causes the pressure in the first pipette 25 to be positive, and the first pipette 25 releases the holding of the cell 100. The cell 100 is placed in the successful cell region. The control unit 46A drives the sample stage 22 again and moves the tip of the first pipette 25 to the vicinity of the untreated cell region where the untreated cells 100 are placed. At Step ST42, when determined that the injection operation was failed (No at Step ST42), the control unit 46A drives the sample stage 22 and moves the cell 100 after injection operation to the failure cell region. The control unit 46A stops the suction pump 29 of the first manipulator 14 and stops the suction of the first pipette 25. This causes the pressure in the first pipette 25 to be positive, and the first pipette 25 releases the holding of the cell 100. The cell 100 is placed in the successful cell region. The control unit 46A drives the sample stage 22 again and moves the tip of the first pipette 25 to the vicinity of the untreated cell region where the untreated cells 100 are placed.

After Step ST44 and Step ST46, at Step ST48, the control unit 46A increments the value of the counter of the manipulation execution number N by one and stores it as N=N+1 in the storage unit 46B of the controller 43. At Step ST50, the control unit 46A determines whether the manipulation execution number N has reached the manipulation termination number Ne. At Step ST50, when determined that the manipulation execution number N is smaller than the manipulation termination number Ne (No at Step ST50), the process returns to Step ST14 and repeatedly performs the holding operation for another cell 100, the detection operation of the cell 100 and the nucleolus 114, the injection operation into the nuclear membrane 112, and the placement operation of the cell 100. At Step ST50, when the manipulation execution number N is greater than or equal to the manipulation termination number Ne (Yes at Step ST50), the manipulations for the predetermined number of cells 100 are finished and a series of operations is terminated.

Because the captured image of the camera 18 is an image captured by imaging the X-Y plane at the focus position, the positions in the Z-direction between the tip of the second pipette 35 and the nucleolus 114 may not overlap. In this case, as the tip of the second pipette 35 is not inserted into the vicinity of the nucleolus 114, a failure of the injection is assumed. In the present embodiment, when the injection was failed (No at Step St42), the cell 100 being held is moved to the failure cell region and the operation to the failed cell 100 is aborted. However, for example, the failed cell 100 may be moved to the untreated cell region and the process may return to Step ST14. For example, at Step ST16, the same cell 100 may be held by changing the posture or a different cell 100 may be held. As for the cell 100 for which the injection was failed, the operator may determine it, or the control unit 46A may determine it based on a predetermined condition.

As described above, the manipulation system 10 of the present embodiment includes the sample stage 22 configured such that a minute object is placed thereon, the first manipulator 14 including the first pipette 25 for holding the minute object, the second manipulator 16 including the second pipette 35 for operating the minute object that is held on the first pipette 25, the microscope unit 12 (imaging unit) for imaging the minute object, and the controller 43 (control device) that controls the sample stage 22, the first pipette 25, the second pipette 35, and the microscope unit 12, and the controller 43 moves the tip of the second pipette 35 from the certain insertion start position D of the minute object to the certain push-in position P at a constant speed or the first acceleration $V_{low}$, and after a predetermined time, moves the tip of the second pipette 35 from the push-in position P to the certain manipulation execution position IJ at the second acceleration $V_{high}$ greater than the first acceleration $V_{low}$.

Accordingly, because the minute object is pressed at low speed until the tip of the second pipette 35 reaches the push-in position P from coming in contact with the minute object, the minute object is not pierced by the second pipette 35 but deformed. The sufficiently deformed minute object, by being pressed at high speed, results in local destruction due to an impact load and is pierced. According to such a manipulation system 10, the piercing can be performed easily without damaging other tissues of the minute object. As a result, regardless of the degree of skill and technique of the operator, manipulation can be performed efficiently and suitably while suppressing damage to the minute object at the time of manipulation.

In the manipulation system 10 of the present embodiment, the controller 43 determines the manipulation execution position IJ on the basis of the image data of the microscope unit 12. According to such a manipulation system 10, because the manipulation execution position IJ is determined based on the captured image data, the manipulation can be performed on the minute object efficiently and suitably, regardless of the degree of skill and technique of the operator.

In the manipulation system 10 of the present embodiment, the controller 43 determines the insertion start position D on the basis of the image data of the microscope unit 12 and the manipulation execution position IJ. According to such a manipulation system 10, because the insertion start position D is determined based on the captured image data and the manipulation execution position IJ that is determined based on the image data, the minute object can be pierced efficiently and suitably, regardless of the degree of skill and technique of the operator.

In the manipulation system 10 of the present embodiment, the controller 43 determines the push-in position P on the basis of the image data of the microscope unit 12 and the manipulation execution position IJ. According to such a manipulation system 10, because the push-in position P is determined based on the captured image data and the manipulation execution position IJ that is determined based on the image data, the minute object can be pierced efficiently and suitably, regardless of the degree of skill and technique of the operator.

In the manipulation system 10 of the present embodiment, the minute object is the cell 100. Accordingly, because the cell membrane 102 is pressed at low speed until the tip of the second pipette 35 reaches the push-in position P from coming in contact with the cell membrane 102 of the cell 100, the cell membrane 102 is not pierced by the second pipette 35 but deformed. The cell membrane 102, when sufficiently pressed, is in a hardened state due to the tensile force. The cell membrane 102 in a hardened state, by being pressed at high speed, results in local destruction due to an impact load and is pierced. According to such a manipulation system 10, the cell membrane 102 can be pierced easily without damaging other tissues in the cell 100. As a result, regardless of the degree of skill and technique of the operator, manipulation can be performed efficiently and suitably while suppressing damage to the cell 100 at the time of manipulation.

In the manipulation system 10 of the present embodiment, the controller 43 detects the position of the nucleolus 114 of the cell 100 on the basis of the image data of the microscope unit 12. According to such a manipulation system 10, because the position of the nucleolus 114 of the cell 100 is detected based on the captured image data, the nucleolus 114 can be detected efficiently and suitably, regardless of the degree of skill and technique of the operator.

In the manipulation system 10 of the present embodiment, the controller 43 determines the manipulation execution position IJ on the basis of the position of the nucleolus 114. According to such a manipulation system 10, because the manipulation execution position IJ is determined based on the position of the nucleolus 114 detected from the captured image data, the manipulation can be performed on the minute object efficiently and suitably, regardless of the degree of skill and technique of the operator.

In the manipulation system 10 of the present embodiment, the manipulation execution position IJ is outside the nucleolus 114. According to such a manipulation system 10, by setting the manipulation execution position IJ outside the nucleolus 114, injection operation can be performed without coming in contact with the nucleolus 114 with the tip of the second pipette 35 when inserting the second pipette 35. Thus, in injection operation, damage to the cell 100 can be suppressed.

In the manipulation system 10 of the present embodiment, the manipulation execution position IJ is a position offset from the center C2 of the nucleolus. According to such a manipulation system 10, the tip of the second pipette 35 can be prevented from damaging the nucleolus 114 when inserting the second pipette 35. Thus, in injection operation, damage to the cell 100 can be suppressed.

In the manipulation system 10 of the present embodiment, the distance in the intersecting direction orthogonal to the insertion direction of the second pipette 35 between the center C2 of the nucleolus 114 and the manipulation execution position IJ is greater than the radius r of the nucleolus 114. According to such a manipulation system 10, because the manipulation execution position IJ can be set outside the nucleolus 114, injection operation can be performed without coming in contact with the nucleolus 114 with the tip of the second pipette 35 when inserting the second pipette 35. Thus, in injection operation, damage to the cell 100 can be suppressed.

A driving method of the manipulation system 10 of the present embodiment is a drive method of the manipulation system 10 including the sample stage 22 configured such that the cell 100 is placed thereon, the first manipulator 14 including the first pipette 25 for holding the cell 100, and the second manipulator 16 including the second pipette 35 for operating the cell 100 that is held on the first pipette 25, and includes Step ST22 of moving the tip of the second pipette 35 to the certain insertion start position D of the cell 100, Step ST24 of moving the tip of the second pipette 35 from the insertion start position D to the certain push-in position P at a constant speed or the first acceleration $V_{low}$, and after a predetermined time, Step ST26 of moving the tip of the second pipette 35 from the push-in position P to the certain manipulation execution position IJ at the second acceleration $V_{high}$ greater than the first acceleration $V_{low}$.

Accordingly, because the minute object is pressed at low speed until the tip of the second pipette 35 reaches the push-in position P from coming in contact with the minute object, the minute object is not pierced by the second pipette 35 but deformed. The sufficiently deformed minute object, by being pressed at high speed, results in local destruction due to an impact load and is pierced. According to such a manipulation system 10, the piercing can be performed easily without damaging other tissues of the minute object. As a result, regardless of the degree of skill and technique of the operator, manipulation can be performed efficiently and suitably while suppressing damage to the minute object at the time of manipulation.

The manipulation system 10 and the driving method of the manipulation system 10 of the present embodiment may be modified as appropriate. For example, it is preferable that the shapes and the like of the first pipette 25, the second pipette 35, and the like be changed as appropriate, depending on the type of minute object and the operation to the minute object. In the respective operations of the holding operation of a minute object, the detection operation of the certain manipulation target position, the injection operation, and the placement operation of the minute object, as appropriate, a part of the procedure may be omitted, or the procedure may be replaced and executed.

REFERENCE SIGNS LIST

10 MANIPULATION SYSTEM
11 SAMPLE HOLDING MEMBER
12 MICROSCOPE UNIT
14 FIRST MANIPULATOR
16 SECOND MANIPULATOR
18 CAMERA
20 MICROSCOPE
22 SAMPLE STAGE
24 FIRST PIPETTE HOLDING MEMBER
25 FIRST PIPETTE
26 X-Y AXIS TABLE
28 Z-AXIS TABLE
29 SUCTION PUMP
30, 32 DRIVE DEVICE
34 SECOND PIPETTE HOLDING MEMBER
35 SECOND PIPETTE
36 X-Y AXIS TABLE
38 Z-AXIS TABLE
39 INJECTION PUMP
40, 42 DRIVE DEVICE
43 CONTROLLER (CONTROL DEVICE)
43A IMAGE INPUT UNIT
43B IMAGE PROCESSOR
43C IMAGE OUTPUT UNIT
43D POSITION DETECTOR
44, 54 MICRO-MOTION MECHANISM
44a PIEZOELECTRIC ACTUATOR
45 DISPLAY UNIT
46A CONTROL UNIT
46B STORAGE UNIT
47 JOYSTICK
47A BUTTON
49 INPUT UNIT
80, 82 ROLLER BEARING
80a, 82a INNER RING
80b, 82b OUTER RING
80c, 82c BALL
81 FOCUSING MECHANISM
84 HOLLOW MEMBER

84a FLANGE PORTION
86 LOCKNUT
87 HOUSING
88 LID
90 SPACER
92 PIEZOELECTRIC ELEMENT
100 CELL
102 CELL MEMBRANE
110 NUCLEUS
112 NUCLEAR MEMBRANE
114 NUCLEOLUS
C1, C2 CENTER
R, r RADIUS
IP INITIAL POSITION
D INSERTION START POSITION
P PUSH-IN POSITION
IJ MANIPULATION EXECUTION POSITION
L0 INITIAL DISTANCE
L PUSH-IN AMOUNT
α, β OFFSET AMOUNT

The invention claimed is:

1. A manipulation system comprising:
a sample stage configured such that a minute object is placed thereon;
a first manipulator including a first pipette for holding the minute object;
a second manipulator including a second pipette for operating the minute object that is held on the first pipette;
an imager configured to image the minute object; and
a controller configured to control the sample stage, the first pipette, the second pipette, and the imager, wherein
the controller moves a tip of the second pipette from a certain insertion start position of the minute object to a certain push-in position at a constant speed or a first acceleration, and after a predetermined time, moves the tip of the second pipette from the push-in position to a certain manipulation execution position at a second acceleration greater than the first acceleration,
the minute object is a cell,
the controller detects a position of a nucleolus of the cell based on image data of the imager, and
a distance in an intersecting direction orthogonal to an insertion direction of the second pipette between a center of the nucleolus and the manipulation execution position is greater than a radius of the nucleolus.

2. The manipulation system according to claim 1, wherein the controller determines the manipulation execution position based on image data of the imager.

3. The manipulation system according to claim 1, wherein the controller determines the insertion start position based on image data of the imager and the manipulation execution position.

4. The manipulation system according to claim 1, wherein the controller determines the push-in position based on image data of the imager and the manipulation execution position.

5. The manipulation system according to claim 1, wherein the controller determines the manipulation execution position based on the position of the nucleolus.

6. The manipulation system according to claim 1, wherein the manipulation execution position is outside the nucleolus.

7. The manipulation system according to claim 1, wherein the manipulation execution position is a position offset from a center of the nucleolus.

8. A driving method of a manipulation system including a sample stage configured such that a cell is placed thereon, a first manipulator including a first pipette for holding the minute object, and a second manipulator including a second pipette for operating the cell that is held on the first pipette, the driving method comprising:
moving a tip of the second pipette to a certain insertion start position of the cell;
moving the tip of the second pipette from the insertion start position to a certain push-in position at a constant speed or a first acceleration; and
after a predetermined time, moving the tip of the second pipette from the push-in position to a certain manipulation execution position at a second acceleration greater than the first acceleration,
wherein the controller detects a position of a nucleolus of the cell based on image data of the imager, and
wherein a distance in an intersecting direction orthogonal to an insertion direction of the second pipette between a center of the nucleolus and the manipulation execution position is greater than a radius of the nucleolus.

* * * * *